United States Patent
Hu

(10) Patent No.: US 9,573,890 B2
(45) Date of Patent: *Feb. 21, 2017

(54) PROCESS FOR PRODUCING TAURINE

(71) Applicant: VITAWORKS IP, LLC, North Brunswick, NJ (US)

(72) Inventor: Songzhou Hu, Princeton, NJ (US)

(73) Assignee: Vitaworks IP, LLC, North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/228,539

(22) Filed: Aug. 4, 2016

(65) Prior Publication Data

US 2016/0340300 A1    Nov. 24, 2016

Related U.S. Application Data

(63) Continuation-in-part of application No. 14/120,651, filed on Jun. 12, 2014, now Pat. No. 9,428,451, which is a continuation-in-part of application No. 14/120,046, filed on Apr. 18, 2014, now Pat. No. 9,428,450.

(51) Int. Cl.
*C07C 303/32* (2006.01)
*C07C 303/02* (2006.01)
*C07C 303/44* (2006.01)

(52) U.S. Cl.
CPC ........... *C07C 303/32* (2013.01); *C07C 303/02* (2013.01); *C07C 303/44* (2013.01)

(58) Field of Classification Search
None
See application file for complete search history.

(56) References Cited

U.S. PATENT DOCUMENTS

| 1,932,907 | A | * | 10/1933 | Nicodemus | ........... C07C 309/14 562/102 |
| 1,999,614 | A | * | 4/1935 | Ossenbeck | ........... C07C 309/14 562/104 |
| 2,820,818 | A | | 1/1958 | Sexton | |
| 8,609,890 | B1 | | 12/2013 | Hu | |
| 2014/0121405 | A1 | * | 5/2014 | Chen | ..................... C07C 303/18 562/104 |
| 2015/0210633 | A1 | | 7/2015 | Hu | |

FOREIGN PATENT DOCUMENTS

| CN | 101486669 A | 7/2009 |
| CN | 101508657 A | 8/2009 |
| CN | 101508658 A | 8/2009 |
| CN | 101508659 A | 8/2009 |
| DE | 219023 A3 | 2/1985 |
| WO | 0177071 A1 | 10/2001 |

OTHER PUBLICATIONS

Abstract of CN101508657.*
Abstract of CN101508658.*
Abstract of CN 101508659.*
Abstract of CN 101486669.*
International Search Report for corresponding International Application No. PCT/CN2015/000232, mailed Jul. 1, 2015.
USPTO Non-Final Office Action for corresponding U.S. Appl. No. 15/228,568 dated Oct. 5, 2016.
USPTO Non-Final Office Action for corresponding U.S. Appl. No. 14/120,651 dated Mar. 15, 2016.

\* cited by examiner

*Primary Examiner* — Karl J Puttlitz
(74) *Attorney, Agent, or Firm* — Graham Curtin, P.A.

(57) ABSTRACT

There is disclosed a process for producing taurine by the ammonolysis of alkali isethionate in the presence of alkali ditaurinate or alkali tritaurinate, or their mixture, to inhibit the formation of byproducts and to continuously convert the byproducts of the ammonolysis reaction to alkali taurinate. The production yield is increased to from 90% to nearly quantitative. The ammonolysis reaction is catalyzed by alkali salts of hydroxide, sulfate, sulfite, phosphate, or carbonate.

10 Claims, No Drawings

PROCESS FOR PRODUCING TAURINE

CROSS REFERENCE TO RELATED APPLICATIONS

This application is a continuation-in-part of application Ser. No. 14/120,651, filed on Jun. 12, 2014, which is a continuation-in-part of application Ser. No. 14/120,046, filed on Apr. 18, 2014, both of which are incorporated here by reference.

TECHNICAL FIELD

The present invention relates to a process for the production of taurine from alkali isethionate in a high overall yield (i.e., greater than 90% to nearly quantitative) by carrying out the ammonolysis reaction of alkali isethionate to alkali taurinate in the presence of alkali ditaurinate or alkali tritaurinate, or their mixture.

BACKGROUND OF THE INVENTION

Taurine can be referred to as 2-aminoethanesulfonic acid and is one of the amino sulfonic acids found in the tissues of many animals. Taurine is an extremely useful compound with beneficial pharmacological effects, such as detoxification, fatigue-relief, and nourishing and tonifying effects. As a result, taurine finds wide applications as an essential ingredient for human and animal nutrition.

Taurine is currently produced in an amount of over 50,000 tons per year from either ethylene oxide or monoethanolamine. At the present time, most taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e., hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under described conditions.

Therefore, the problems encountered in the production of taurine from the ethylene oxide process arise from the ammonolysis of sodium isethionate and from the separation of taurine from sodium sulfate.

U.S. Pat. No. 1,932,907 discloses that sodium taurinate is obtained in a yield of 80%, when sodium isethionate undergoes ammonolysis reaction in a molar ratio of 1:6.8 for 2 hrs at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD219023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tri-taurinate.

WO01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

It is therefore concluded from the foregoing references that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins involving a strongly acid ion exchange resin in hydrogen form, and then an anion exchange resin in basic form. This process is complicated and requires the use of a large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities, which are identified as a mixture of sodium ditaurinate and sodium tritaurinate.

In the co-pending application Ser. No. 14/120,046, a novel process is disclosed for converting alkali ditaurinate or alkali tritaurinate, or their mixture, to alkali taurinate.

It is, therefore, an object of the present invention to disclose a process for the production of taurine from alkali isethionate in a high overall yield (i.e., greater than 90% to nearly quantitative). According to the process of the present invention, a solution of alkali ditaurinate or alkali tritaurinate, or their mixture, is mixed with alkali isethionate to increase the yield of the ammonolysis reaction by inhibiting the formation of alkali ditaurinate and tritaurinate byproducts and by converting the byproducts to alkali taurinate in the presence of one or more catalysts.

DESCRIPTION OF THE INVENTION

The present invention relates to a process for the production of taurine by the ammonolysis reaction of alkali isethionate in the presence of alkali ditaurinate or alkali tritaurinate, or their mixture, to inhibit the formation of byproducts, to increase the production yield, and to greatly reduce the waste discharge from the production process.

The process according to the present invention starts with mixing a solution of alkali ditaurinate or alkali tritaurinate, or their mixture, with alkali isethionate, followed by addition of an excess of ammonia. The ammonolysis is carried out at a temperature from 160° C. to 260° C. under the pressure from autogenous to 260 bars for 1 to 6 hours.

After the ammonolysis reaction, excess ammonia is dispelled from the reaction solution and reclaimed for reuse. A solution of alkali taurinate is obtained, along with alkali ditaurinate, alkali tritaurinate, and a trace amount of unreacted alkali isethionate.

The strongly basic solution is neutralized with an acid to pH 5-9 to yield a crystalline suspension of taurine in a solution of alkali salt, alkali ditaurinate, alkali tritaurinate, and a small amount of unreacted alkali isethionate. The initial suspension is optionally concentrated, then cooled to 28 to 35° C., to crystallize taurine. Taurine is obtained by means of solid-liquid separation.

The ratio of alkali ditaurinate, alkali tritaurinate, or their mixture, in relation to alkali isethionate can be varied from 0.01 to 10 by weight, preferably 0.1 to 1, more preferably 0.2-0.5, most preferably 0.3-0.4.

When the ratio is low, i.e., <0.1, a large amount of alkali isethionate is converted to alkali ditaurinate, instead of desired alkali taurinate, thus lowering the production yield and efficiency. When the ratio is too large, i.e., >1.0, the amount of the recycling byproducts becomes excessively large and the production capacity is lowered. Moreover, the cyclic process is not steady as the byproduct is indeed converted alkali taurinate.

Useful and effective catalysts are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate can be one component or a combination of two or more components. Catalysts exogenous to the reaction system can be used, but catalysts inherently present in the production process are preferred. When sulfuric acid is used as a neutralizing acid, alkali salts of sulfate are preferred. Alkali salts of sulfite are preferred in the sulfur dioxide process.

Preferable catalysts are alkali hydroxide and the most preferable catalyst is sodium hydroxide.

The amount of the catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

The acid used in the neutralization process is selected from hydrochloric acid, hydrobromic acid, sulfuric acid, nitric acid, phosphoric acid, and organic carboxylic acids containing one to six carbons. Sulfuric acid is most preferably used.

Tables I to III demonstrate the effectiveness of the presence of alkali ditaurinate or alkali tritaurinate, or their mixture, on the ammonolysis of alkali isethionate to alkali taurinate, respectively. It becomes apparent that the conversion of alkali isethionate to alkali taurinate can reach nearly quantitative yield under disclosed conditions.

Table IV shows the effect of a different catalyst on the ammonolysis of alkali isethionate to alkali taurinate. When no catalyst is added to the ammonolysis reaction, low conversion of alkali isethionate is observed.

The process according to the present invention can be carried out discontinuously, semi-continuously, and continuously.

EXAMPLES

The following examples illustrate the practice of this invention but are not intended to limit its scope.

Example 1

This set of examples relates to the ammonolysis of sodium isethionate in the presence of sodium ditaurinate and in the presence of sodium hydroxide.

All examples are for 0.05 mole of sodium isethionate, dissolved in 35 mL of 20% aqueous ammonia solution in a molar ratio of 1:8 for sodium isethionate to ammonia. Calculated amount of sodium ditaurinate and sodium hydroxide is then added to the solution. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−Added Ditaurine]/[Sodium Isethionate]

TABLE I

Ammonolysis of Sodium Isethionate in the Presence of Sodium Ditaurinate

| Ex | Ditaurinate/Isethionate (ratio by weight) | NaOH/Isethionate (ratio by weight) | Taurinate (molar yield %) | Di + Tritaurinate (molar yield %) |
|---|---|---|---|---|
| 1 | 0 | 0.01 | 75 | 24 |
| 2 | 0.1 | 0.01 | 84 | 15 |
| 3 | 0.2 | 0.01 | 86 | 14 |
| 4 | 0.3 | 0.01 | 87 | 13 |
| 5 | 0.3 | 0.02 | 91 | 9 |
| 6 | 0.3 | 0.03 | 93 | 7 |
| 7 | 0.3 | 0.04 | 95 | 5 |
| 8 | 0.3 | 0.05 | 98 | 2 |
| 9 | 0.5 | 0.15 | 112 | −12 |
| 10 | 1.0 | 0.20 | 145 | −45 |

Example 2

This set of examples relates to the ammonolysis of sodium isethionate in the presence of sodium tritaurinate and in the presence of sodium hydroxide.

All examples are for 0.05 mole of sodium isethionate, dissolved in 35 mL of 20% aqueous ammonia solution in a molar ratio of 1:8 for sodium isethionate to ammonia. Calculated amount of sodium tritaurinate and sodium hydroxide is then added to the solution. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−Added Tritaurine]/[Sodium Isethionate]

TABLE II

Ammonolysis of Sodium Isethionate in
the Presence of Sodium Tritaurinate

| Ex | Tritaurinate/Isethionate (ratio by weight) | NaOH/Isethionate (ratio by weight) | Taurinate (molar yield %) | Di + Tritaurinate (molar yield %) |
|---|---|---|---|---|
| 11 | 0 | 0.01 | 76 | 24 |
| 12 | 0.1 | 0.01 | 83 | 16 |
| 13 | 0.2 | 0.01 | 86 | 14 |
| 14 | 0.3 | 0.01 | 87 | 13 |
| 15 | 0.3 | 0.02 | 88 | 11 |
| 16 | 0.3 | 0.03 | 94 | 6 |
| 17 | 0.3 | 0.04 | 94 | 5 |
| 18 | 0.3 | 0.05 | 98 | 2 |
| 19 | 0.5 | 0.15 | 121 | −20 |
| 20 | 1.0 | 0.20 | 151 | −49 |

Example 3

This set of examples relates to the ammonolysis of sodium isethionate in the presence of a mixture of sodium ditaurinate and sodium tritaurinate obtained from the mother liquor of taurine crystallization and in the presence of sodium hydroxide and sodium sulfate.

All examples are for 0.05 mole of sodium isethionate, dissolved in 35 mL of 20% aqueous ammonia solution in a molar ratio of 1:8 for sodium isethionate to ammonia. Calculated amount sodium hydroxide is then added to the solution. A mixture of sodium ditaurinate and sodium tritaurinate, obtained from the crystallization mother liquor described as in application Ser. No. 14/120,046 is used. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−(Added Di+Tritaurine)]/[Sodium Isethionate]

TABLE III

Ammonolysis of Sodium Isethionate in the Presence of a
Mixture of Sodium Ditaurinate and Sodium Tritaurinate

| Ex | (Di + Tritaurinate)/Isethionate (ratio by weight) | NaOH/Isethionate (ratio by weight) | Taurinate (molar yield %) | Di + Tritaurinate (molar yield %) |
|---|---|---|---|---|
| 21 | 0 | 0.01 | 81 | 19 |
| 22 | 0.1 | 0.01 | 84 | 16 |
| 23 | 0.2 | 0.01 | 87 | 12 |
| 24 | 0.3 | 0.01 | 87 | 13 |
| 25 | 0.3 | 0.02 | 88 | 11 |
| 26 | 0.3 | 0.03 | 95 | 4 |
| 27 | 0.3 | 0.04 | 96 | 4 |
| 28 | 0.3 | 0.05 | 98 | 2 |
| 29 | 0.5 | 0.15 | 126 | −26 |
| 30 | 1.0 | 0.20 | 154 | −53 |

Example 4

This set of examples shows the effect of a different catalyst on the ammonolysis of sodium isethionate in the presence of a mixture of sodium ditaurinate and sodium tritaurinate obtained from the mother liquor of taurine crystallization.

All examples are for 0.05 mole of sodium isethionate, dissolved in 35 mL of 20% aqueous ammonia solution in a molar ratio of 1:8 for sodium isethionate to ammonia. Calculated amount catalyst and a mixture of sodium ditaurinate and sodium tritaurinate, obtained from the crystallization mother liquor described as in application Ser. No. 14/120,046, are added to the solution. The ratio of (di+tritaurinate)/isethionate by weight is fixed at 0.3. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

Di+Tritaurinate Yield (%)=[Di+Tritaurine−(Added Di+Tritaurine)]/[Sodium Isethionate]

TABLE IV

Effect of Catalyst on Ammonolysis of Sodium Isethionate in the Presence
of a Mixture of Sodium Ditaurinate and Sodium Tritaurinate

| Ex | Catalyst | Catalyst/Isethionate (ratio by weight) | Taurinate (molar yield %) | Di + Tritaurinate (molar yield %) |
|---|---|---|---|---|
| 31 | None | 0 | 55 | 12 |
| 32 | Sodium carbonate | 0.15 | 96 | 4 |
| 33 | Sodium sulfite | 0.15 | 95 | 4 |
| 34 | Potassium hydroxide | 0.10 | 97 | 3 |
| 35 | Potassium carbonate | 0.15 | 94 | 6 |
| 36 | Potassium sulfite | 0.10 | 94 | 6 |
| 37 | Lithium hydroxide | 0.03 | 95 | 4 |
| 38 | Lithium carbonate | 0.10 | 93 | 7 |
| 39 | Sodium phosphate | 0.15 | 97 | 3 |
| 40 | Potassium phosphate | 0.15 | 96 | 4 |
| 41 | Potassium acetate | 0.20 | 96 | 4 |
| 42 | Sodium acetate | 0.20 | 96 | 4 |

It will be understood that the foregoing examples and explanation are for illustrative purposes only and that various modifications of the present invention will be self-evident to those skilled in the art. Such modifications are to be included within the spirit and purview of this application and the scope of the appended claims.

What is claimed is:
1. A process for producing taurine from alkali isethionate, comprising:
   (a) mixing alkali isethionate with a solution of alkali ditaurinate, alkali tritaurinate, or their mixture in the presence of one or more catalysts;
   (b) adding an excess of ammonia to the (a) and subjecting the solution to ammonolysis reaction to yield a mixture of alkali taurinate, alkali ditaurinate, and alkali tritaurinate;
   (c) removing excess ammonia and neutralizing with an acid to obtain a crystalline suspension of taurine; and
   (d) separating taurine by means of solid-liquid separation.
2. The process according to claim 1, wherein alkali taurinate and alkali tritaurinate are produced from diethanolamine and triethanolamine, respectively.
3. The process according to claim 1, wherein a mixture of alkali ditaurinate and alkali tritaurinate is the byproduct of the ammonolysis reaction of alkali isethionate.

4. The process according to claim 1, wherein an acid is selected from hydrochloric acid, hydrobromic acid, sulfuric acid, nitric acid, and organic carboxylic acids.

5. The process according to claim 1, wherein the mother liquor after separating taurine and alkali salt is continuously recycled and mixed with a new batch of alkali isethionate for the ammonolysis reaction.

6. The process according to claim 1, one or a combination of two or more catalysts for the ammonolysis reaction is selected from alkali salts of hydroxide, carbonate, sulfate, sulfite, phosphate, and nitrate.

7. The process according to claim 1, wherein the production yield of taurine is greater than 95%, to nearly quantitative.

8. The process according to claim 1, wherein the alkali metals are lithium, sodium, or potassium.

9. The process according to claim 1, wherein the production yield of taurine is greater than 85%.

10. The process according to claim 1, wherein the production yield of taurine is greater than 90%.

\* \* \* \* \*

(12) INTER PARTES REVIEW CERTIFICATE (2007th)
United States Patent
Hu

(10) Number: US 9,573,890 K1
(45) Certificate Issued: Apr. 1, 2021

(54) PROCESS FOR PRODUCING TAURINE

(71) Applicant: Songzhou Hu

(72) Inventor: Songzhou Hu

(73) Assignee: VITAWORKS IP, LLC

Trial Number:

IPR2018-01768 filed Sep. 28, 2018

Inter Partes Review Certificate for:

Patent No.: 9,573,890
Issued: Feb. 21, 2017
Appl. No.: 15/228,539
Filed: Aug. 4, 2016

The results of IPR2018-01768 are reflected in this inter partes review certificate under 35 U.S.C. 318(b).

INTER PARTES REVIEW CERTIFICATE
U.S. Patent 9,573,890 K1
Trial No. IPR2018-01768
Certificate Issued Apr. 1, 2021

AS A RESULT OF THE INTER PARTES REVIEW PROCEEDING, IT HAS BEEN DETERMINED THAT:

Claims 1 and 3-10 are cancelled.

\* \* \* \* \*